United States Patent [19]

Christgau et al.

[11] Patent Number: 5,830,734
[45] Date of Patent: Nov. 3, 1998

[54] ENZYME WITH ACETYL ESTERASE ACTIVITY

[75] Inventors: Stephen Christgau, Gentofte; Thomas Sandal; Markus Sakari Kauppinen, both of Copenhagen; Torben Halkier, Frederiksberg; Henrik Dalbøge, Virum, all of Denmark

[73] Assignee: Novo Nordisk A/S, Bassvaerd, Denmark

[21] Appl. No.: 578,592

[22] PCT Filed: Jul. 13, 1994

[86] PCT No.: PCT/DK94/00285

§ 371 Date: Jan. 4, 1996

§ 102(e) Date: Jan. 4, 1996

[87] PCT Pub. No.: WO95/02689

PCT Pub. Date: Jan. 26, 1995

[30] Foreign Application Priority Data

Jul. 13, 1993 [DK] Denmark ................... 839/93

[51] Int. Cl.⁶ ............... C12Q 1/44; C12N 9/18; C07G 17/00; D21C 3/00
[52] U.S. Cl. ............. 435/197; 435/18; 435/101; 435/196; 435/267; 435/274; 435/278
[58] Field of Search ..................... 435/101, 196, 435/225, 267, 274, 278, 197, 18, 19; 426/635

[56] References Cited

U.S. PATENT DOCUMENTS 5,681,732  10/1997  De Graaff et al. ............ 435/197

OTHER PUBLICATIONS

Tenkanen et al. (1993) Appl Microb Biotech 39:159–165 "Enzymatic Deacylation of Galactoglucomannans".
Khan et al (1990) Enzyme Microb Technol 12:127–137 "Comparison of Natural Hemicellulose and Chemically Acetylated Xylan as Subsyrates . . . .".
Samson (1994) "Taxonomy–Current Concepts of Aspersillus Systematics" pp. 1–19 in Aspergillus (ed. J. Smith), Plenum Press, New York.

*Primary Examiner*—Rebecca E. Prouty
*Assistant Examiner*—Elizabeth Slobodyansky
*Attorney, Agent, or Firm*—Steven T. Zelson; Cheryl H. Agris

[57] ABSTRACT

An isolated and purified acetyl esterase with activity towards acetylated xylan and acetylated mannan obtained from *Aspergillus aculeatus* and having amino acid sequence that comprises Seq ID No 1. An enzyme can be used for the modification of plant cell wall components.

11 Claims, 5 Drawing Sheets

ENZYME WITH ACETYL ESTERASE ACTIVITY

FIELD OF INVENTION

The present invention relates to enzymes with acetyl esterase activity, a method of producing the enzymes, and an enzyme preparation containing one or more of the enzymes.

BACKGROUND OF THE INVENTION

Many polysaccharides can exist in acetylated forms in various biological plant materials (mainly in xylan, mannan and pectin polymers) [1]. The biological significance of the acetyl groups is not fully understood. It is known that the acetyl group often protects the polysaccharide from degradation by hydrolytic enzymes. Hence, deacetylation of these polysaccharides is necessary in order to achieve partial or complete enzymatic breakdown of the acetylated polysaccharide [2–4].

Accordingly, it is contemplated [2,3] that acetyl esterases are important enzymes for the food industry, primarily in fruit and vegetable processing such as fruit juice production, wine making or pectin extraction, where their ability to modify acetylated polysaccharides to a readily degradable form may be utilised.

It is known that many fungi contain enzymes capable of deacetylating acetylated polysaccharides, which enzymes are commonly designated acetyl esterases. Some fungal acetyl esterases have been purified [5–9]. However, the study of these enzymes have been hampered by the lack of well-characterized homogeneous substrates, and by the difficult and time consuming assays for measuring acetate release. Any industrial use of these enzymes has not been described.

WO 92/19728 describes a rhamnogalacturonan acetyl esterase isolated from the fungal species *Aspergillus aculeatus*. This enzyme is specific for acetylated galacturonic acid residues in hairy regions of pectin. EP 507 369 discloses a DNA sequence encoding an acetyl xylan esterase isolated from *Aspergillus niger*.

For many purposes, it would be desirable to provide acetyl esterases in a form essentially free from other components. In this way, it would be possible to produce enzyme preparations adapted to specific purposes, such preparations either containing a single acetyl esterase or arbitrary combinations thereof, and optionally containing other polysaccharide degrading enzymes. To serve this end, it is convenient to provide single-component acetyl esterases by recombinant DNA techniques.

SUMMARY OF THE INVENTION

It has now surprisingly been found that the fungal species *A. aculeatus*, in addition to the above mentioned rhamnogalacturonan acetylesterase, produces a number of novel acetyl esterases with interesting enzymatic activities. Despite the fact that these enzymes are produced in very low amounts (constituting less than 0.1% of the total enzyme production), the present inventors have succeeded in purifying and characterizing the novel enzymes.

Accordingly, the present invention relates to novel enzymes having acetyl esterase activity and in particular to single-component acetyl esterases.

More specifically, in a first aspect the present invention relates to an enzyme with acetyl esterase activity, which enzyme comprises the amino acid sequence shown in SEQ ID No. 1, in which x designates any amino acid residue.

In the present context the term "with acetyl esterase activity" is used to define a group of enzymes, the members of which have the common characteristic of being capable of cleaving the acetyl esterase substrate p-nitrophenol-acetate (PNP-acetate) by the procedure given in the Materials and Methods section below. Furthermore, they may in some cases be able to act on other acetylated non-saccharide substrates. These enzymes are commonly termed acetyl esterases. It will be understood that the natural substrate for each of the acetyl esterases disclosed herein may vary between different acetylated polysaccharides, as exemplified by acetylated mannans, acetylated xylans, acetylated rhamnogalacturonans and acetylated pectins.

In the course of the research leading to the present invention is it was surprisingly found that different acetyl esterases isolated from *A. aculeatus* comprise the partial amino acid sequence shown in SEQ ID No. 1. The presence of this sequence may be a characteristic feature of acetyl esterases, in particular of acetyl esterases produced by *A. aculeatus* or by other related organisms. As stated above, x may be any amino acid sequence which in the present context is intended to be understood to comprise alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

In a second aspect the present invention relates to an enzyme with acetyl esterase activity, which enzyme is active towards acetylated xylan as well as acetylated mannan. As far as the present inventors are aware there has been no previous disclosure of an enzyme having activity towards both of these substrates. Thus, acetyl esterases are known to be very specific as they only deacetylate one type of acetylated carbohydrate. The acetyl esterase according to this aspect of the invention is advantageous in that it can be used for more than one type of substrate.

In the present context the terms "activity towards acetylated xylan" and "activity towards acetylated mannan" are intended to indicate that the enzyme is capable of hydrolyzing the ester linkage found between acetyl groups and xylan and mannan, respectively. A suitable assay for determining activity towards the two substrates are given in the Materials and Methods section below.

In a further aspect the invention relates to an enzyme with acetyl esterase activity, which enzyme is immunologically reactive with an antibody raised against a purified acetyl esterase derived from *Aspergillus aculeatus*, CBS 101.43 and having a molecular weight of about 44 or 35 kDa.

The *A. aculeatus* acetyl esterase having a molecular weight of about 44 kDa or about 35 kDa is as defined herein. It will be understood that the exact value obtained for the molecular weight of a given enzyme will depend on the method used for its determination. Thus, variations in the actual value determined may occur, even when only a slightly different Mw-determination method is used and/or when the Mw-determination is carried out by two different persons. Thus, the molecular weights of enzymes given herein should be evaluated on this basis and interpreted rather as a range around the actual value stated, than an exact value. If the molecular weight of the enzyme is determined by any other suitable method known in the art (e.g. mass spectromety, gel filtration or sedimentation), than that actually used in the present context (which is further described in the Materials and Methods section below) one may thus expect a different Mw to be obtained than that actually stated in the present application.

In the present context, the term "derived from" is intended not only to indicate an acetyl esterase produced by strain CBS 101.43, but also an acetyl esterase encoded by a DNA sequence isolated from strain CBS 101.43 and produced in a host organism transformed with said DNA sequence.

In a still further aspect the invention relates to an enzyme with acetyl esterase activity, which enzyme is encoded by a DNA sequence comprising the DNA sequence shown in SEQ ID No. 4.

It will be understood that also an enzyme encoded by a DNA sequence comprising an analogue of the DNA sequence shown in SEQ ID No. 4 is to be considered within the present invention.

In the present context the term "analogue" is understood to include any DNA sequence which encodes an enzyme with acetyl esterase activity and which is at least 70% homologous to the DNA sequence shown in SEQ ID No. 4, including a partial sequence of the DNA sequence shown in SEQ ID No. 4. The analogous DNA sequence may be a DNA sequence which hybridizes to the same probe as the DNA coding for the acetyl esterase under the following conditions: presoaking in 5×SSC and prehybridizing for 1 h at ~40° C. in a solution of 5×SSC, 5×Denhardt's solution, 50 mM sodium phosphate, pH 6.8, and 50 μg of denatured sonicated calf thymus DNA, followed by hybridization in the same solution supplemented with 50 μCi 32-P-dCTP labelled probe for 18 h at ~40° C. followed by washing three times in 2×SSC, 0.2% SDS at 40° C. for 30 minutes. The analogous DNA sequence is preferably at least 80% such as at least 90% homologous to the sequence shown in SEQ ID No. 4, preferably at least 95% homologous to said sequence.

The analogous DNA sequence may, e.g., be isolated from another organism or may be one prepared on the basis of the amino acid sequence shown in any of SEQ ID Nos. 1–3, such as by introduction of nucleotide substitutions which do not give rise to another amino acid sequence of the acetyl esterase but which correspond to the codon usage of the host organism into which the DNA construct is introduced or nucleotide substitutions which do give rise to a different amino acid sequence and therefore, possibly, a different protein structure which might give rise to an acetyl esterase mutant with different properties than the native enzyme. Other examples of possible modifications are insertion of one or more nucleotides into the sequence, addition of one or more nucleotides at either end of the sequence, or deletion of one or more nucleotides at either end or within the sequence.

In still further aspects, the present invention relates to an enzyme preparation useful for the degradation of plant cell wall components, said preparation being enriched in an enzyme with acetyl esterase activity as described above, and to various uses of the enzyme or enzyme preparation.

DETAILED DESCRIPTION OF THE INVENTION

Figure 1:
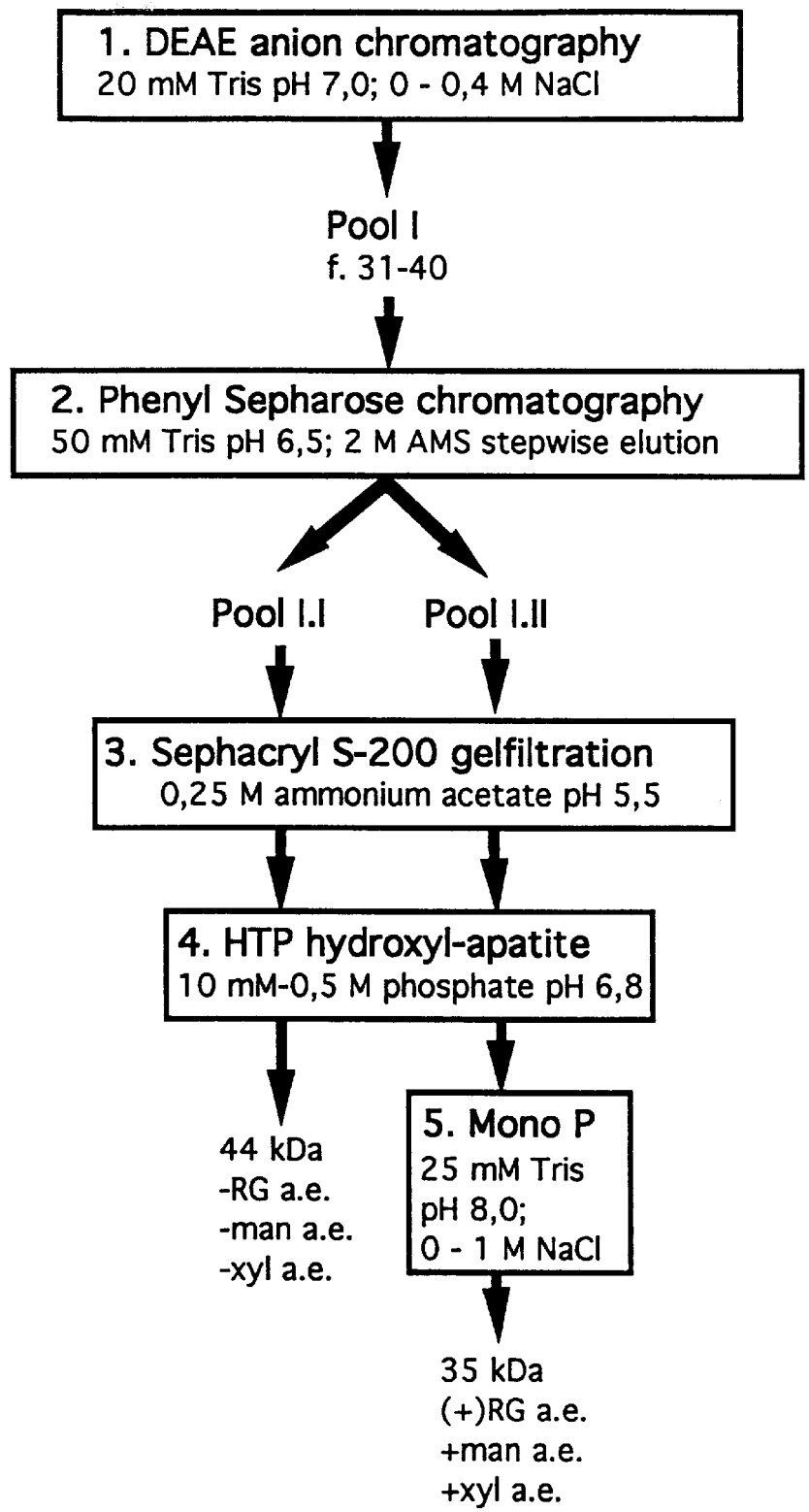

According to one embodiment, the enzyme of the invention comprising the consensus amino acid sequence shown in SEQ ID No. 1, is one which comprises the N-terminal amino acid sequence shown in SEQ ID No. 2. This enzyme is termed acetyl esterase I in the following disclosure.

In the present context the term "N-terminal amino acid sequence" is intended to be understood in its conventional meaning, i.e. as the N-terminal amino acid sequence of the mature (secreted and processed) enzyme, i.e. the N-terminal sequence remaining after any signal sequence or prosequence have been cleaved off.

Acetyl esterase I of the invention is preferably encoded by a DNA sequence comprising the DNA sequence shown in SEQ ID No. 4 or an analogue of said DNA sequence, which is at least 70% homologous, preferably at least 80%, and more preferably at least 90% homologous with said DNA sequence.

Preferably, acetyl esterase I has a molecular weight of about 44 kDa, a pI in the range of 4.4–5.1 and/or a pH optimum in the range of about 6.0–9.0, such as in the range of about 7.0–7.5 when determined under the conditions described herein.

Acetyl esterase I of the invention has been found to be substantially devoid of activity towards acetylated xylan, acetylated mannan and/or acetylated rhamnogalacturonan (as determined by the assays described in the Materials and Methods section herein). Furthermore, acetyl esterase I have been found to be devoid of lipase activity.

Another enzyme of the present invention is one, which comprises the N-terminal amino acid sequence shown in SEQ ID No. 3, in which x may be any amino acid residue. This enzyme is termed acetyl esterase II in the following disclosure.

Acetyl esterase II of the invention has been found to be active towards acetylated xylan or acetylated mannan, and substantially devoid of activity towards acetylated rhamnogalacturonan. In fact, acetyl esterase II of the invention is believed to be the first disclosed enzyme having activity towards both acetylated xylan and acetylated mannan.

At present, it is preferred that acetyl esterase II of the invention is one, in which x of the amino acid sequence shown above is a threonine residue.

Acetyl esterase II of the present invention preferably has a pI in the range of 4–5, such as about 4.5, and/or a molecular weight of about 35 kDa.

It will be understood that homologues of the above identified enzymes are to be considered to be within the present invention. In the present context the term "homologue" is intended to indicate an enzyme with acetyl esterase activity which has an N-terminal amino acid sequence differing in one or more amino acid residues from the sequence shown in SEQ ID No. 2 or 3, respectively, without substantially impairing the characteristic acetyl esterase activity of the enzyme. For instance, the homologue may be a naturally occurring or genetically engineered variant of acetyl esterase I or II of the invention, e.g. prepared by suitably modifying the DNA sequence encoding the amino acid sequence, resulting in the addition of one or more amino acid residues to either or both the N- and C-terminal end of the sequence, substitution of one or more amino acid residues at one or more different sites in the amino acid sequence, deletion of one or more amino acid residues at either or both ends of or at one or more sites in the amino acid sequence, or insertion of one or more amino acid residues at one or more sites in the amino acid sequence.

Preferably, the N-terminal amino acid sequence of the homologous enzyme is at least 70% homologous, such as at least 80%, 90% or 95% homologous with the N-terminal amino acid sequence shown in SEQ ID No. 2 or 3, respectively.

By the present invention it is possible to provide the acetyl esterase in a highly purified form, i.e. greater than 80% pure, and more preferably greater than 90% pure as determined by SDS gel electrophoresis as described in the Materials and Methods section herein.

While it is contemplated that enzymes of the invention with acetyl esterase activity may be derivable from any source, including plants and mammals, it is presently preferred that the enzyme is of microbial origin.

In the present context, the term "microbial origin" is intended to include bacteria and fungi (such as filamentous fungi or yeasts). The term "derivable" is intended to include that the enzyme may be recovered from any of the origins mentioned or may be encoded by and expressed from a DNA sequence isolated from or prepared on the basis of DNA from the origin in question.

In particular, the enzyme of the invention may be derivable from a fungus, more specifically from a strain of Aspergillus, in particular *A. aculeatus* or *A. niger*, a strain of Trichoderma, in particular *T. harzianum, T. reesie,* or a strain of Fusarium, in particular *F. oxysporum,* or from a strain of Saccharomyces, in particular *S. cerevisiae*.

As an example, enzymes of the invention with acetyl esterase activity may be recovered from a culture of any suitable organism, e.g. *Aspergillus aculeatus,* by purification methods known in the art involving ultrafiltration, column chromatography, gel filtration and the like, and suitable combinations of any of these treatments. The protein-containing fractions obtained by these procedures may subsequently be assayed for acetyl esterase activity. A more detailed description of an entire purification scheme is given in Example 1 below.

Although the above outlined procedure may be used for producing enzymes of the present invention, it is presently preferred to employ recombinant DNA techniques for this purpose. Accordingly, it is preferred that the enzyme of the invention is produced by expression from a DNA sequence encoding the enzyme, which is isolated from a cDNA or genomic library of a suitable organism, e.g. as mentioned above. A preferred example of a suitable organism is *Aspergillus aculeatus,* CBS 101.43, publicly available from the Centraalbureau voor Schimmelcultures, Delft, NL.

The DNA sequence coding for the enzyme may for instance be isolated by screening a cDNA library of a suitable organism, e.g. *Aspergillus aculeatus,* and selecting for clones hybridizing with a DNA probe prepared on the basis of an amino acid sequence of said enzyme, such as the ones described above. The hybridization may be carried out under conditions known in the art, e.g. the conditions described above in connection with analogous DNA.

Alternatively, the DNA sequence may be isolated by screening a cDNA or genomic library of any of the organisms mentioned above, in particular a strain of *A. aculeatus,* and selecting for clones expressing acetyl esterase activity as defined above. However, this latter approach may be hampered when the cDNA or genomic library is prepared in cells, which themselves express acetyl esterase activity, and thereby give rise to false positive screening results. Especially, eukaryotic cells are expected to express acetyl esterase activity, which, when PNP-acetate is used as a substrate, will result in false positive results.

The appropriate DNA sequence selected by either of the above methods may then be isolated from the clone by standard procedures.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the acetyl esterase enzyme should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the acetyl esterase, the promoter and the terminator, respectively, and to insert them into suitable vectors are well known to persons skilled in the art (cf., for instance, Sambrook et al., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed acetyl esterase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

In addition to being used in the preparation of an acetyl esterase of the invention, a DNA sequence encoding such acetyl esterase may be used for inactivating or destroying genes encoding acetyl esterases. Thus, for some applications, it may be important that acetyl groups are present on the polysaccharide substrate to be used, rather than being removed by the action of an acetyl esterase. This may be the case for some applications where a gum is to be used as substrate. Accordingly, the action of acetyl esterases on such substrates may be undesirable.

It is therefore contemplated that a DNA sequence encoding an acetyl esterase of the invention (such as the DNA sequence shown in SEQ ID No. 4) or a part thereof may be used to avoid the presence of acetyl esterase activity in polysaccharide degrading enzyme preparations to be used for applications, in which the presence of acetyl groups on the substrate are desirable. More specifically, it is contemplated that a DNA sequence encoding an acetyl esterase of the invention may be used for disrupting or inactivating an acetyl esterase gene present and active in an organism which is to be used as a producer of polysaccharide degrading enzymes, substantially free from or comprising only a minor amount of an acetyl esterase enzyme.

The inactivation may conveniently be accomplished by preparing an antisense sequence of the acetyl esterase gene and using this antisense sequence for inactivating the acetyl esterase gene(s) in question in accordance with well-known antisense technology. Hereby, novel enzyme producing organisms, such as microorganisms, may be produced which are capable of producing polysaccharide degrading enzymes with a minor amount of (or substantially without) an undesirable acetyl esterase activity.

In a still further aspect, the present invention relates to an enzyme preparation useful for the degradation or modification of plant cell wall components, said preparation being enriched in an enzyme with acetyl esterase activity as described above.

The enzyme preparation having been enriched with an enzyme of the invention may e.g. be an enzyme preparation comprising multiple enzymatic activities, in particular an enzyme preparation comprising multiple plant cell wall degrading enzymes such as Pulpzyme, Gamanase, Pectinex®, Pectinex Ultra SP®, Celluclast or Celluzyme (all available from Novo Nordisk A/S). In the present context, the term "enriched" is intended to indicate that the acetyl esterase activity of the enzyme preparation has been increased, e.g. with an enrichment factor of at least 1.1, conveniently due to addition of an enzyme of the invention prepared by the method described above.

Alternatively, the enzyme preparation enriched in an enzyme with acetyl esterase activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to an acetyl esterase of the invention, contain one or more other plant cell wall degrading enzymes, for instance those with cellulytic, xylanolytic, mannanolytic or pectinolytic activities such as α-arabinosidase, xylanase, α-glucoronisidase, β-xylosidase, mannanase, β-mannosidase, α-galactosidase, arabinanase, rhamnogalacturonase, galactanase, polygalacturonase, pectin lyase, pectate lyase, glucanase, α-galacturonisidase, or pectin methylesterase.

The additional enzyme(s) may be producible by means of a microorganism belonging to the genus Aspergillus, preferably *Aspergillus niger, Aspergillus aculeatus, Aspergillus awamori* or *Aspergillus oryzae,* or Trichoderma.

The enzyme preparation according to the invention is preferably used as an agent for degradation or modification of plant cell wall materials and any xylan or mannan-containing material originating from plant cell walls.

Examples are given below of preferred uses of the enzyme preparation of the invention. The dosage of the enzyme preparation of the invention and other conditions under which the preparation is used may be determined on the basis of methods known in the art.

Many polysaccharides are known to be acetylated, e.g. acetylated xylans from hardwood, softwood or cereals, acetylated galactomannans and galactoglucomannans from softwood, acetylated pectin from e.g. sugar beets, acetylated rhamnogalacturonan and acetylated xyloglucan from dicotyledons, and acetylated gums like gum karaya (from sterculia tree) and is xanthan gum (bacterial gum).

The acetylation of carbohydrates often hinders (fully or partially) the degradation of the carbohydrate by endoacting enzymes such as the degradation of acetylated xylan with xylanases or the degradation of acetylated galactomannan with mannanases.

Accordingly, it is advantageous to use an acetyl esterase of the invention in combination with xylanases without other xylanolytic enzymes (especially β-xylosidases) or with limited activity of other xylanolytic enzymes to degrade xylans to oligosaccharides. Such oligosaccharides may be used as bulking agents.

The degradation of xylan by an acetyl esterase of the invention in combination with a xylanase containing enzyme preparation is facilitated by full or partial removal of the sidebranches of xylan. Arabinose sidegroups can be removed by a mild acid treatment or by alpha-arabinosidases and the glucuronic acid sidebranches can be removed by alpha-glucuronisidases.

The oligomers released by the combined action of an acetyl esterase and a xylanase, or of an acetyl esterase, a xylanase and a sidebranch-hydrolysing enzyme as mentioned above can be further degraded to free xylose (and other monosaccharides) by beta-xylosidases. The released xylose may be converted to other compounds like furanone flavours.

The acetyl esterase of the present invention can be used in combination with a mannanase without other mannanolytic enzymes or with limited activity of other mannanolytic enzymes to degrade mannans (including galactomannans, glucomannans, and galactoglucomannans) for production of oligosaccharides. The oligosaccharides may be used as bulking agents. The degradation of mannan by an acetyl esterase of the invention and a mannanase containing enzyme preparation is facilitated by full or partial removal of mannan sidebranches. For instance, the galactose sidebranches of mannan may be removed by alpha-galactosidase.

The oligomers with are released by the acetyl esterase and mannanase or by a combination of acetyl esterase, mannanase and alpha-galactosidase as mentioned above can be further degraded to free mannose by beta-mannosidase (and beta-glucosidase for glucomannans and galactoglucomannans).

Acetyl esterases of the present invention may, in combination with xylanolytic enzymes, be used for modification of animal feed and may exert their effect either in vitro (by modifying components of the feed) or in vivo. The acetyl esterases are particularly suited for addition to animal feed compositions containing high amounts of acetylated xylans, e.g. feed containing grass, or leaves of cereals or maize.

Acetyl esterases of the present invention may in combination with xylanases and/or mannanases be used in the paper and pulp industry, e.g. to improve the bleachability or drainability of lignocellulosic pulp.

Plant material may be treated with an acetyl esterase of the invention in combination with other enzymes in order to improve different kinds of processing, facilitate purification or extraction of different component like carbohydrates, improve the feed value, decrease the water binding capacity, improve the degradability in waste water plants, improve the conversion of e.g. grass and corn to ensilage, or to hydrolyse various plant cell wall-derived materials or waste materials, e.g. from paper production, or agricultural residues such as wheat-straw, corn cobs, whole corn plants, nut shells, grass, vegetable hulls, bean hulls, spent grains, sugar beet pulp, and the like.

The acetyl esterase preparation of the invention may be used to deacetylate carbohydrates in order to change properties thereof, such as the rheology, the stabilizing ability or the hydrophobicity of the carbohydrates. Examples are deacetylation of xylans and mannans. The carbohydrate acetyl esterase preparation to be used for the above purpose is preferable essentially free from activities with can depolymerize said carbohydrates.

Furthermore, in systems with low water activity acetyl esterases of the invention may be used to esterify, e.g. acetylate (by ester synthesis or transesterification), carbohydrates like xylans and mannans. The thereby formed acetylated carbohydrates may be more acetylated than naturally occurring carbohydrates, and will have new properties like increased hydrophobicity and thereby improved ability to emulsify and/or stabilize fat-containing emulsions.

The enzyme preparation of the invention may be used for degrading plant cell wall polysaccharides in the food industry, primarily in fruit and vegetable processing such as fruit juice production or wine making, and in the paper and pulp industry. Furthermore, the enzyme preparation may be used for modification or degradation of gums, e.g. used in food applications. Examples of such gums are gum Karaya (from sterculia tree), gum arabic, and in particular Locust Bean Gum (carob tree), guar gum and xanthan gum (bacterial gum).

The invention is further illustrated in the drawing, in which

Figure 2:
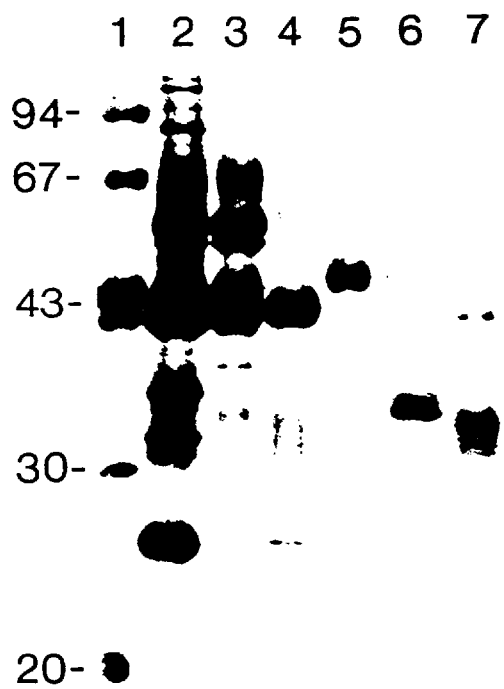
Figure 3:
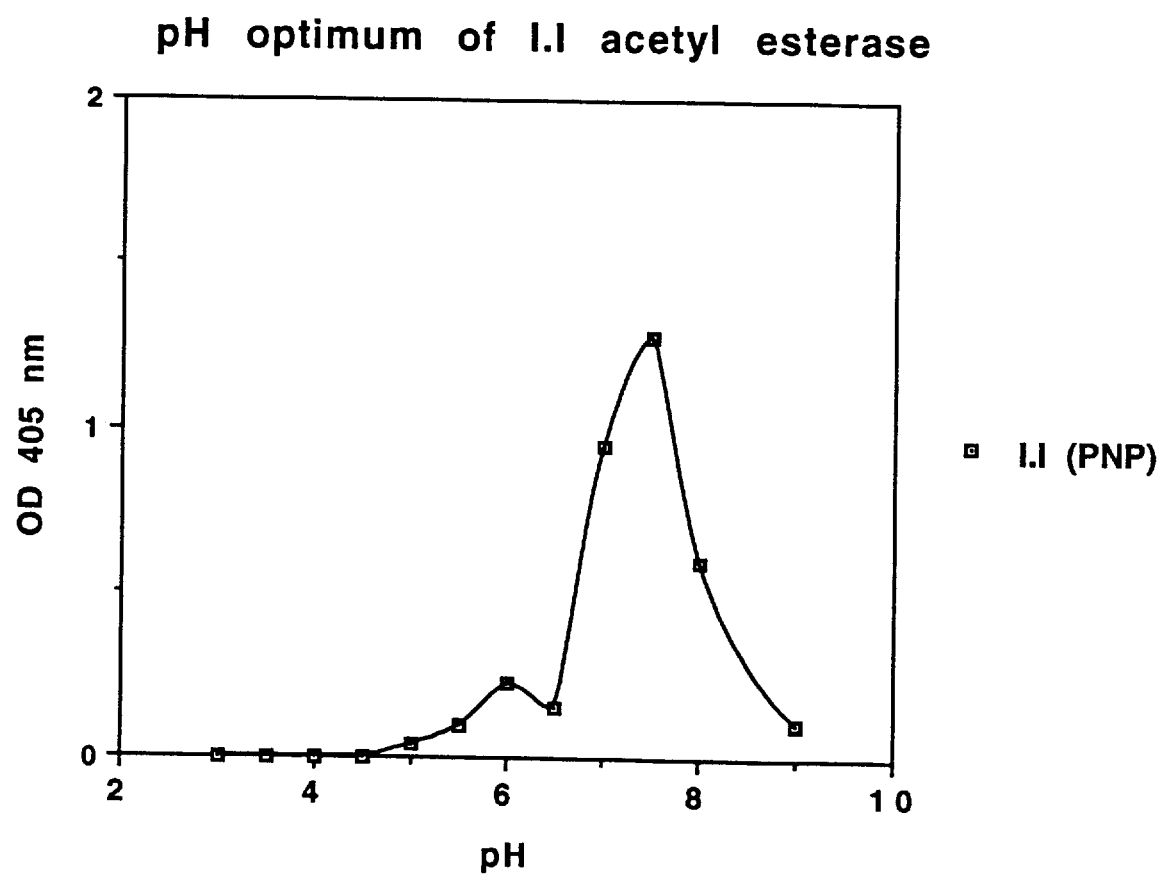
Figure 4:
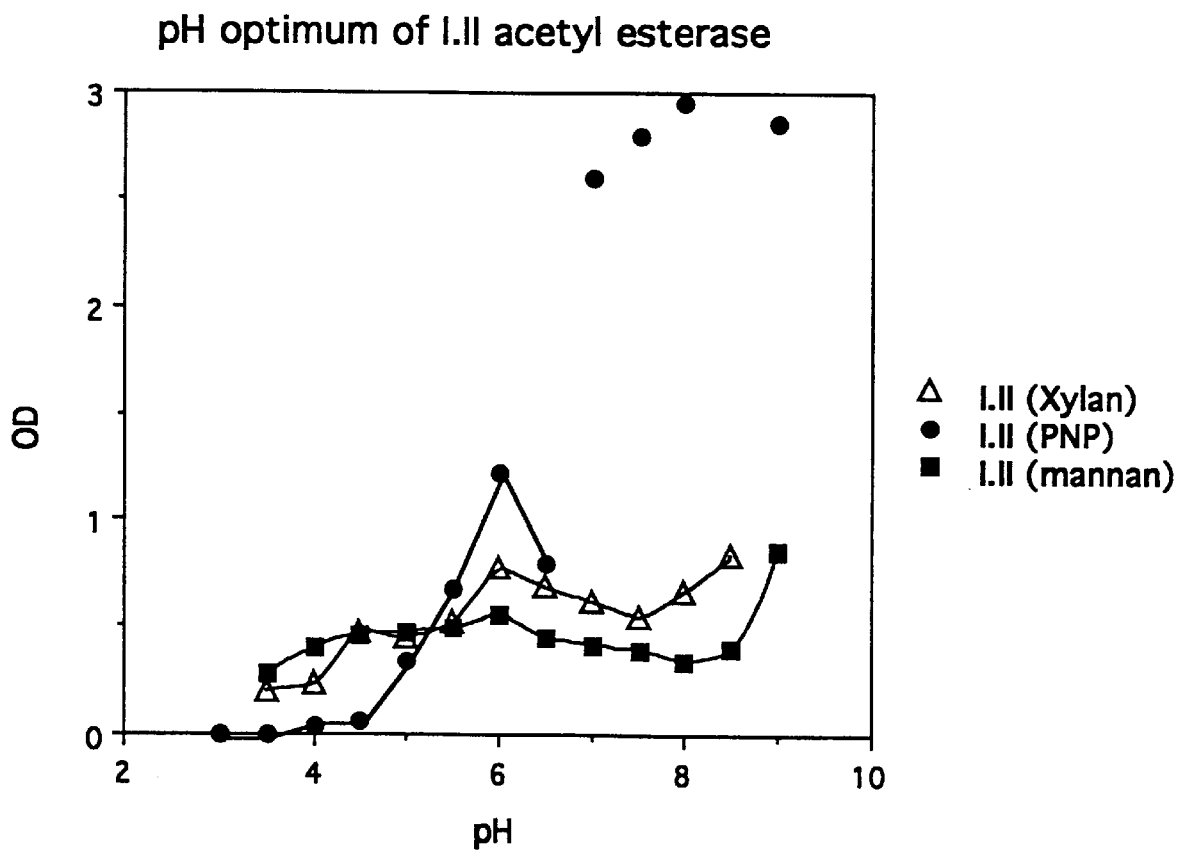
Figure 5:
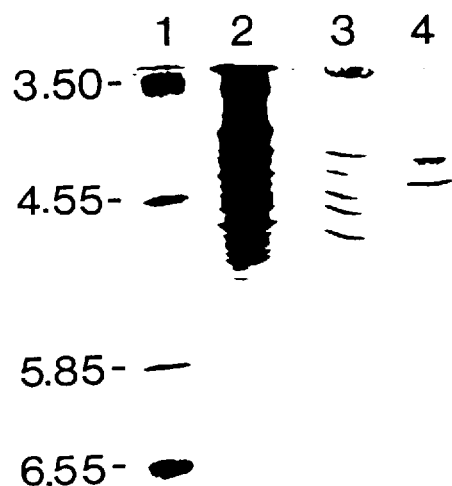

FIG. 1 is a flowsheet illustrating the purification procedure used for isolating enzymes of the invention, FIG. 2 a silver stained SDS-PAGE gel of purified acetylesterases isolated from the A.aculeatus supernatant described herein. The proteins were separated on a 12% T SDS-PAGE gel and silverstained as described in the materials and methods section herein. Lane 1: molecular weight markers (Phosphorylase B: 94 kDa, BSA: 67 kDa, Ovalbumin: 43 kDa, Carbonic anhydrase: 30 kDa, STI: 20.1 kDa). Lane 2: 10 µg of A. aculeatus supernatant. Lane 3: 20 µg Pool I. Lane 4: 10 µg of a side-fraction obtained from anion exchange purification. Lane 5: 0.8 µg Pool I.I. Lane 6: 0.07 µg Pool I.II. Lane 7: 1.2 µg purified rhamnogalacturonan acetyl esterase (WO 92/19728);

FIG. 3 illustrates the pH optimum of the acetyl esterase recovered from pool I.I determined as described in the materials and methods section below;

FIG. 4 the pH optimum of the acetyl esterase recovered from pool I.II as determined on PNP acetate, acetylated mannan and acetylated xylan; and FIG. 5 the iso-electric point of an enzyme of the invention determined by isoelectric focusing. Lane 1: isoelectric point of marker Amyloglycosidase (pI 3.5), trypsin inhibitor (pI 4.55), bovine carbonic anhydrase (pI 5.85), human carbonic anhydrase (pI 6.55). Lane 2: 10 µg A. aculeatus culture supernatant. Lane 3: 1 µg Pool I.I. Lane 4: 1 µg Pool I.II.

The invention is described in further detail in the following examples which are not in any way intended to limit the scope of the invention as claimed.

MATERIALS AND METHODS

Donor organism and fermentation: *Aspergillus aculeatus*, strain CBS 101.43, was grown in a medium containing 12% w/w of soy-cake and 1.5% potassium phosphate with a pH lower than 5.0 in a 40 $m^3$ aerated continuously stirred fermenter. The pH was kept at approx. 4.2 during the fermentation, and potato starch was added continuously during the fermentation. The resulting culture supernatant was filtered, centrifugated and concentrated in a 20 kDa UF filter to approx. 100 mg/ml protein.

PNP-acetyl esterase activity: The activity was measured by incubating a sample of the purified enzyme in 500 µl of 1.6 mM PNP-acetate (Sigma, St. Louis, U.S.A.); 20 mM citrate pH 5.5 and quantifying the amount of PNP released by measuring $OD_{405}$ after addition of 100 µl 1M Tris, pH 7.0. One unit is defined as the activity which releases 1 µmole PNP/min. at 40° C.

Acetyl esterase assay (Boehringer Mannheim assay): The assay is performed as described in the manufacturers manual.

The substrate solutions to be used in the assay are prepared by dissolving the acetylated polysaccharide substrate to a 1% solution/suspension in reagent grade water.

65 µl of the substrate solution is added to 30 µl of 0.3M buffer of an appropriate pH (i.e. Tris buffer pH 6.5 for Pool I.I and I.II acetyl esterases). Finally 5 µl enzyme solution is added (as well as blanks with 5 µl water).

The samples are incubated 1 hour at 37° C. on a shaking table and then heated to 95° C. for 15 min. to inactivate the enzyme.

10 µl of this solution is used to measure acetate content by the Boehringer Manheim assay.

Acetylated substrates:

Acetylated Rhamnogalacturonan (Modified Hairy Regions)

The substrate was obtained from Golden Delicious Apples by partial pectinolytic degradation with a pectinase preparation (Pectinex AR, Novo-Nordisk), followed by centrifugation, aroma-stripping and ultrafiltration on a MW 60,000 Da. cut-off BX3 polysulfone membrane (Paterson Candy Ltd.) The retentate was dialysed against water and lyophilized. The MHR fraction represents 1,7% of the apple solids and approximately 4% of the saccharides are acetylated.

Acetylated Mannan

The substrate was kindly provided by Jürgen Puls (Hamburg, FRG). It was isolated from Norwegian Bruce (Picia abes) by delignifying sawdust with chlorite according to standard procedures, followed by DMSO extraction of hemicellulose. Extracted polysaccharides were separated by anion exchange on a DEAE sepharose column, and the fractions containing mannan were collected.

Acetylated Xylan

Acetylated xylan was obtained as a non-dialysable fraction of water soluble polysaccharide produced by steam extraction of birchwood as described in reference 6 (Kormelink & Voragen). It contained 70.6% total sugars and 10.6% acetyl (based on dry matter).

SDS-page electrophoresis was performed in a Mini-Leak 4 electrophoresis unit (Kem-En-Tec, Denmark) as a modified version of the Laemli procedure [16]. Isoelectric focusing was carried out on Ampholine PAG plates pH 3.5–9.5 (Pharmacia, Sweden) on a Multiphor electrophoresis unit according to the manufactures instructions. Gels were either silverstained essentially as described in [11] or coomassie stained.

Determination of pI: The isoelectric points were determined by electrophoresis on a Pharmacia Ampholine PAG plate (pH 3.5–9.5) according to the manufacturers instructions. After electrophoresis the gel was silver stained as described below.

Protein assay: The BioRad protein assay was used.

Determination of pH optimum:

with PNP-acetate

The purified enzyme (2–5 µg) was incubated with 2 mM PNP-acetate in 50 mM citrate-phosphate buffer of various pH. After 25 min incubation, the PNP release was quantified by measuring $OD_{405nm}$ in 0.2M Tris pH 7.0. Control samples containing PNP-acetate and buffer, but no enzyme were included and the absorbance measured in these samples were subtracted from the enzyme containing samples.

with acetylated polysaccharides

For determination of activity of the enzyme on acetylated polysaccharides, the sample was incubated with a 1% substrate solution in 0.1M citrate/phosphate buffer of various pH, and after 30 min incubation, the released acetate was measured by the Boehringer Mannheim assay. Control samples without enzyme were included, and subtracted from the enzyme containing samples.

Amino acid sequencing: The purified enzymes were run on an SDS-PAGE as described above and electro-blotted to a PVDF-membrane (Immobillon, Milipore, U.S.A.) using standard procedures. The electro-blotted proteins were subjected to N-terminal amino acid sequence determination on an Applied Biosystems 473A sequencer operated in accordance with the manufacturers instructions.

mRNA preparation: mRNA may be isolated from *Aspergillus aculeatus,* CBS 101.43, grown as described above, by harvesting mycelia after 3–5 days' growth, immediately freezing in liquid nitrogen and storing at –80° C.

Construction of an *A. aculeatus* cDNA library in *E. coli:* was performed substantially as described in WO 92/19728, the contents of which is hereby incorporated by reference. More specifically, total RNA is extracted from homogenized *A. aculeatus* mycelium using methods as described by Boel et al. (EMBO J., 3: 1097–1102, 1984) and Chirgwin et al. (Biochemistry (Wash), 18: 5294–5299, 1979). Poly(A)-containing RNA is obtained by two cycles of affinity chromatography on oligo(dT)-cellulose as described by Aviv and Leder (PNAS, USA 69:1408–1412, 1972). cDNA is synthesized with the use of a cDNA synthesis kit from Invitrogen according to the manufacturer's description.

Identification of *A. aculeatus* acetyl esterase specific cDNA recombinants: was performed by use of synthetic oligodeoxyribonucleotides prepared on the basis of the determined amino acid sequences of the acetyl esterases or by use of immunological screening procedures. These procedures are described in detail in WO 92/19728.

Construction of an Asperaillus expression vector: may be performed by inserting a DNA sequence obtained as described above in the expression vector pHD414 described in WO 92/19728. The resulting expression plasmid may be amplified in *E. coli* in accordance with well-known procedures, and subsequent transformed into *A. oryzae* or *A. niger* according to the general procedure described below.

Transformation of *Aspergillus oryzae* or *Aspergillus niger* (*general procedure*)

100 ml of YPD (Sherman et al., Methods in Yeast Genetics, Cold Spring Harbor Laboratory, 1981) is inoculated with spores of *A. oryzae* or *A. niger* and incubated with shaking at 37° C. for about 2 days. The mycelium is harvested by filtration through miracloth and washed with 200 ml of 0.6M $MgSO_4$. The mycelium is suspended in 15 ml of 1.2M $MgSO_4$. 10 mM $NaH_2PO_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH=7.0. Centrifugation is performed for 15 minutes at 100 g and the protoplasts are collected from the top of the $MgSO_4$ cushion. 2 volumes of STC (1.2M sorbitol, 10 mM Tris-HCl, pH=7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 µl of protoplast suspension is mixed with 5–25 µg of the appropriate DNA in 10 µl of STC. Protoplasts are mixed with p3SR2 (an *A. nidulans* amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove Biochem.Biophys.Acta 113 (1966) 51–56) containing 1.0M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Immunological cross-reactivity: Antibodies to be used in determining immunological cross-reactivity may be prepared by use of a purified acetyl esterase. More specifically, antiserum against an enzyme of the invention may be raised by immunizing rabbits (or other rodents) according to the procedure described by N. Axelsen et al. in: *A Manual of quantitative Immunoelectrophoresis,* Blackwell Scientific Publications, 1973, Chapter 23, or A. Johnstone and R. Thorpe, *Immunochemistry in Practice,* Blackwell Scientific Publications, 1982 (more specifically pp. 27–31). Purified immunoglobulins may be obtained from the antisera, for example by salt precipitation (($NH_4)_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

EXAMPLE 1

Purification

The purification of the acetyl esterases was carried out as outlined in FIG. 1.

Initial purification 100 ml of *Aspergillus aculeatus* supernatant obtained as described above were ultrafiltrated in a 200 ml Amicon cell with a 10 kDa membrane. The retentate was diluted 10 times with 20 mM tris pH 7.0, adjusted to a final volume of 50 ml, and applied to a 250 ml DEAE column (50 mm internal diameter) in 20 mM tris pH 7.0 at a flow rate of 4 ml/min. Bound proteins were eluted with a linear gradient from 0.1 to 0.4M NaCl over 200 min., and 10 ml fractions were collected and assayed for PNP-acetyl-esterase activity. One peak of PNP-acetyl esterase activity was eluted (Pool I) as indicated in FIG. 1.

To pool I ammonium sulphate (AMS) was added to a final concentration of 2M and the resulting mixture was applied to a 60 ml Phenyl sepharose column (26 mm internal diameter) in 50 mM tris pH 6.5; 2M AMS at a flow rate of 2 ml/min. Bound proteins were eluted with a step gradient of falling AMS concentration (a decrease of 0.5M AMS per step), and the DEAE pool was separated into two distinct peaks of activity (Pool I.I and Pool I.II).

The pools from the phenyl Sepharose column were purified by gelfiltration on a 500 ml Superdex 6.75 column (26 mm internal diameter) in 0.25M ammonium acetate, pH 5.5, at a flow rate of 1 ml/min. 10 ml fractions were collected and assayed for PNP-acetyl-esterase activity using the above described procedure.

Final Purification of Partially Purified Acetyl Esterase Containing Fractions

Pool I.I (acetyl esterase I):

This pool of activity was ultrafiltrated into 10 mM sodium phosphate pH 6.8, and applied to a 8 ml BioRad HTP hydroxyl apatite column (10 mm internal diameter) at a constant flow rate of 1 ml/min. Bound proteins were eluted with a linear increasing phosphate concentration to 0.5M over 30 min. 5 ml fractions were collected and assayed for PNP-acetyl-esterase activity and protein content (using SDS-PAGE and protein assay). The purified enzyme had a molecular weight of 44 kDa as determined by SDS-PAGE as described above. The purified enzyme did not show any activity towards acetylated xylan, mannan or rhamnogalacturonan.

Pool I.II (acetyl esterase II)

After gelfiltration, a fraction, which has activity on both acetylated mannan and xylan, was obtained. This fraction was ultrafiltrated into 10 mM sodium phosphate pH 6.8 and applied to a 8 ml BioRad HTP hydroxyl apatite column (10 mm internal diameter) at a constant flow rate of 1 ml/min. Bound proteins were eluted with a linear increasing phosphate concentration to 0.5M over 30 min. 5 ml fractions were collected and assayed for PNP-acetyl-esterase activity and protein content (SDS-PAGE and protein assay). The activity was recovered in two fractions, both of which contain a 42 kDa protein and a 35 kDa protein. The 42 kDa protein is assumed to be the polygalacturonase I described in PCT/DK93/00445. The last eluted fraction was ultrafiltrated into 25 mM tris pH 8.0 and is applied on a 1 ml mono-P column at 1 ml/min. Bound proteins were elluted with a linear increasing NaCl gradient from 0 to 0.5M NaCl during 60 min. 2 ml fractions were collected and assayed for PNP-acetyl-esterase activity and protein content (SDS-PAGE and protein assay). The fraction with activity contains one 35 kDa protein which is active on both acetylated mannan and xylan.

In the following table, purification factors and activity of A. aculeatus acetyl esterases obtained during the above described purification procedure are listed. Selected fractions from the purification procedure are shown, as well as the final purified enzyme fractions. The recovery of PNP-acetyl esterase activity was 0.8%. The acetyl esterase activity was measured by the procedure given above.

| Fraction | Protein content | Activity (µmol/min) | Specific activity | Purification factor |
| --- | --- | --- | --- | --- |
| A.a. sup.*) | 10 g | 6320.00 U | 0.632 U/mg | 1.0 |
| Pool I | 950 mg | 2148.00 U | 2.26 U/mg | 3.6 |
| Pool I.I after S-200 | 21 mg | 345.00 U | 16.87 U/mg | 26.7 |
| Pool I.II after S-200 | 192 mg | 574.20 U | 2.47 U/mg | 3.9 |
| Pool I.I | 200 µg | 3.49 U | 17.46 U/mg | 27.6 |
| Pool I.II | 200 µg | 20.00 U | 100.00 U/mg | 158.2 |

*)A. aculeatus supernatant

EXAMPLE 2

Characterization of Purified Acetyl Esterases of the Invention

The pH optimum of the purified acetyl esterases described in Example 1 above was determined using the procedures described in the Materials and Methods section above.

The acetyl esterase isolated from Pool I.I (and having an apparent molecular weight of 44 kDa) was found to have a pH optimum of 7.0–7.5 when using PNP-acetate as a substrate. The enzyme was found to be active from pH 5.0 to pH 9.0. The pH profile is shown in FIG. 3.

The acetyl esterase isolated from Pool I.II was found to have a minor pH optimum of 6.0 and a major pH optimum of pH 7–9 using PNP-acetate as a substrate. However, this high activity at alkaline pH may be an artefact caused by the instability of the substrate above neutral pH. Using acetylated mannan and xylan as substrate a broad pH optimum with a peak at 6.0 was detected. The pH profile is shown in FIG. 4.

The isoelectric points of the two enzymes were determined by use of the procedure described in the Materials and Methods section above. The results are shown in FIG. 5.

The N-terminal amino acid sequence of the two enzymes were determined using the procedure described in the materials and methods section above.

EXAMPLE 3

Generation of a cDNA Probe by Polymerase Chain Reaction

To obtain a cDNA probe for an acetyl esterase from A. aculeatus, a degenerate oligonucleotide (primer AE 1.1/p3; p3γ-5'-TTYGAYTGGGAYWSIAC-3') (SEQ ID NO:6) corresponding to a region in the NH$_2$-terminal sequence of the purified acetyl esterase I was synthesized by incorporating deoxyinosines at the ambiguous position. The primer was used pairwise with the direct (primer #22, 5'-CTGTAATACGACTCACTA-3') (SEQ ID NO:7) and reverse (primer #172 5'-GGGCGTGAATGTAAGCGTGAC-3') (SEQ ID NO:8) pYES 2.0 primers to amplify the target acetyl esterase cDNA from an amplified cDNA library pool containing 7000 clones employing the polymerase chain reaction technique (Ohara et al. 1989). The PCR reactions were carried out in 100 µl PCR buffer (10 mM Tris-HCl, pH 8.3, 50 mM KCl, 1.5 mM MgCl$_2$, 0.01%, Perkin-Elmer, Cetus) containing 550 pmol of sense primer (AE1.1/p3) and 100 pmol of each antisense primer (see above), 1 µg template DNA (Qiagen-purified plasmid DNA) and 200 µM each dNTP using a DNA thermal cycler and 2.5 units of Taq polymerase (Perkin-Elmer, Cetus). Thirty cycles of PCR were performed using a cycle profile of denaturation at 94° C. for 1 minute, annealing at 55° C. for 2 minutes, and extension at 72° C. for 3 minutes.

Ten µl aliquots of the amplification products were analyzed by electrophoresis on 1% agarose gels revealing a 1.5 kb and a 1.0 kb product with one primer pair (AE1.1/p3; pYES reverse primer #172). The DNA fragment of interest was excised from the gel, recovered by electroelution (Sambrook et al. 1989) using type D-0405 seamless dialysis tubing (Sigma), followed by phenol extraction and ethanol precipitation at −20° C. for 12 hours. The PCR product was blunt-ended at 37° C. for 10 minutes in 20 µl buffer (20 mM Tris-acetate, pH 7.9, 10 mM MgAc, 50 mM KAc, 1 mM DTT) containing 50 µM each dNTP and 3 units of T4 DNA polymerase (New England Biolabs). The reaction was stopped by incubation at 70° C. for 5 minutes, chilled on ice for 5 minutes and diluted in 50 µl of kinase buffer (70 mM Tris-HCl, pH 7.6, 10 MM MgCl$_2$, 5 mM DTT) followed by phosphorylation at 37° C. for 30 minutes with T4 polynucleotide kinase (10 U, New England Biolabs) and 1 mM ATP pH 7.0 (Pharmacia), phenol extraction, ethanol precipitation and ligation at 16° C. for 12 hours into Sma I-cut, dephosphorylated pUC18 vector (50 ng per ligation, Pharmacia).

E. coli DH5α was transformed to ampicillin resistance (Hanahan 1985) using 5 µl of the ligation mixture, and 10 clones were analyzed by isolation of plasmid miniprep. DNA (Sambrook et al. 1989), and EcoRI/HindIII digestion of the plasmid subclones, followed by sequencing the ends of the 1.5 kb insert from one subclone (pAE 8.1.1) with universal pUC primers (Sanger et al. 1977). Nucleotide sequence analysis of the pC1AE1 subclone revealed a unique open reading frame which, in addition to the primer encoded amino acids, contained additional residues concurring with the available NH$_2$-terminal sequence from the purified acetyl esterase I.

Isolation and Characterization of a Full-length cDNA Encoding an Acetyl Esterase from A. aculeatus To isolate a full-length cDNA clone for an acetyl esterase, colonies from the cDNA library pool #22 were plated on LB-agar (24×24 cm plate, Nunc) containing ampicillin (100 µg/ml) and replicated on an LB+amp–plate covered with a nylon filter (Hybond-N, Amersham). The purified 1.5 kb acetyl esterase PCR fragment was $^{32}$P-labeled by random-priming as above, and used as a probe in screening the library pool by colony hybridization (Sambrook et al., 1989). The hybridization was carried out in 2×SSC (Sambrook et al. ,1989), 5×Denhardt's solution (Sambrook et al. 1989), 1% (W/V) SDS and 100 µg/ml denatured salmon sperm DNA with a probe concentration of 2.5 ng/ml for 16 hours at 65° C., then in 2×SSC (2×15 minutes), 0.2×SSC, 1% SDS (2×30 minutes), and in 2×SSC (2×15 minutes) followed by autoradiography at −80° C. for 12 hours. Screening of 10,000 colonies from pool 22 yielded 10 putative acetyl esterase I cDNA clones that were colony-purified by two more rounds of hybridizations. One of these clones (designated pC1AE1) was characterized by digesting the plasmid with HindIII and XbaI and sequencing the ends of the 1.4 kb cDNA insert with forward and reverse pYES 2.0 polylinker primers.

The 1.4 kb insert in pC1AE1 contains a 1019 bp open reading frame (ORF) initiating with an ATG codon at nucleotide position 33 and terminating with a TGA stop codon (SEQ ID No. 4). SEQ ID No. 4 shows the nucleotide sequence of the 3'-end of the acetyl esterase cDNA and SEQ ID No. 5 the deduced primary structure of an acetyl esterase from A. aculeatus contemplated to be highly homologous to acetyl esterase I. The ORF is preceded by a 39 bp 5' non-coding region and followed by a 132 bp 3' non-coding region and a poly(A) tail. Comparison of the deduced protein sequence with the NH$_2$-terminal sequence of the purified mature acetyl esterase I reveals that the cDNA encodes a precursor protein containing a 27 residue signal peptide and possibly propeptide.

EXAMPLE 4

In order to express the enzyme in Aspergillus, cDNA is isolated from one or more representatives of each family by digestion with HindIII/XbaI or other appropriate restriction enzymes, size fractionation on a gel and purification and subsequently ligated to pHD414. After amplification in E. coli, the plasmids are transformed into A. oryzae or A. niger according to the general procedure described above.

REFERENCES CITED IN THE SPECIFICATION

1. Carpita, N. C. and D. M. Gibeaut, (1993), "Structural models of primary cell walls in flowering plants: consistency of molecular structure with the physical properties of the walls during growth", The Plant Journal 3(1), 1–30,
2. Sutherland, I. W., (1992), "The role of acylation in exopolysaccharides including those for food use", Food Biotechnology, 6(1), 75–86,
3. McKay, A. M., (1993), "Microbial carboxylic ester hydrolases (EC 3.1.1) in food biotechnology", Letters in Applied Microbiology, 16, 1–6,
4. Dekker, R. F. and G. N. Richards, (1976), "Hemicellulases: Their occurence, purification, properties and mode of action", in Advances in carbohydrate chemistry and biochemistry, R. S. Tipson and D. Horton, Editor, Academic Press: New York. p. 277–352,
5. Ward, O. P. and M. Moo-Young, (1989), "Enzymatic Degradation of Cell Wall and Related Plant Polysaccharides". CRC Critical Reviews in Biotechnology, 8(4): p. 237–274,
6. Searle-van Leeuwen, M. J. F., et al., (1992), "Rhamnogalacturonan acetyl esterase: a novel enzyme from Aspergillus aculeatus, specific for the deacetylation of hairy (ramified) regions of pectin". Appl. Microbiol. Biotechnol., 38: p. 347–349,
7. Kormelink, F. J. M., et al., (1992), "The purification and characterization of an acetyl xylan esterase from Aspergillus niger". J. Biotechnol., 27 267–282,
8. Khan, A. W., K. A. Lamb, and R. P. Overend, (1990), "Comparison of natural hemicellulose and chemically acetylated xylan as substrates for the determination of acetyl-xylan esterase activity in Aspergilli". Enzyme Microb. Technol., 12: p. 127–131,
9. Sundberg, M. and K. Poutanen, (1991), "Purification and properties of two acetylxylan esterases of Tricoderma reesi". Biotechnol. Appl. Biochem., 13: p. 1–11,
10. Biely, P., J. Puls, and H. Schneider (1985), "Acetyl xylan esterases in fungal cellulytic systems".FEBS Lett., 186: p 80–84,
11. Mose Larsen, P., (1981) "An assessment of the potential offered by two-dimensional gel electrophoresis and silverstaining for developmental biology". Dissertation, Århus university.
12. Sambrook, J., Fritsch, E. F. & Maniatis, T. 1989. Molecular Cloning: A Laboratory Manual. Cold Spring Harbor Lab., Cold Spring Harbor, N.Y.
13. Sanger, F., Nicklen, S. & Coulson, A. R. 1977. Proc. Natl. Acad. Sci. U.S.A. 74: 5463–5467.

14. Ohara, O., Dorit, R. L. & Gilbert, W. 1989. Proc. Natl. Acad. Sci. U.S.A. 86:5673–5677.
15. Hanahan, D. 1985. in DNA Cloning, (Glover, D. M., ed.) IRL, Oxford, Vol. 1., pp. 109–135.
16. Laemmli, U. K., 1970, "Cleavage of structural proteins during the assembly of the head of bacteriophage T4"., Nature, 227, p. 680–685
17. Aviv, H. & Leder, P. 1972. Proc. Natl. Acad. Sci. U.S.A. 69: 1408–1412;
18. Becker, D. M. & Guarante, L. 1991. Methods Enzymol. 194: 182–187;
19. Chirgwin, J. M., Przybyla, A. E., MacDonald, R. J. & Rutter, W. J. 1979. Biochemistry 18: 5294–5299;
20. Gubler, U. & Hoffman, B. J. 1983. Gene 25: 263–269.

---

We claim:

1. An isolated and purified enzyme with acetyl esterase activity obtained from a strain of *Aspergillus aculeatus*, which enzyme exhibits activity towards acetylated xylan and acetylated mannan and which enzyme comprises the amino acid sequence shown in SEQ ID No.1, in which Xaa denotes any amino acid residue.

2. The enzyme according to claim 1, which enzyme comprises the N-terminal amino acid sequence shown in SEQ ID No. 3, in which Xaa denotes any amino acid residue.

3. The enzyme according to claim 2, in which Xaa of the N-terminal amino acid sequence is T.

4. The enzyme according to claim 1, which has a pI of about 4–5.

5. The enzyme according to claim 1, which has a molecular weight of about 35 kDa.

6. The enzyme according to claim 1, which enzyme is derivable from *Aspergillus aculeatus*, CBS 101.43.

7. The enzyme according to claim 1, which is encoded by a DNA sequence isolated from a DNA library of *Aspergillus aculeatus*, CBS 101.43.

8. An enzyme preparation useful for the for the treatment of plant cell wall components, said preparation being enriched in an enzyme with acetyl esterase activity according to claim 1.

9. The preparation according to claim 8, which further comprises a xylanase, a mannase, a pectin lyase, a rhamnogalacturonase, a polygalacturonase, arabinase, galactanase, glucanase, and/or pectin methylesterase.

10. A method for degrading or modifying plant material comprising treating said plant material with an amount of the preparation of claim 9 effective to modify or degrade said plant material.

11. The method according to claim 10, in which acetylated xylan and/or acetylated mannan is degraded or modified in said plant material.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

```
Ile  Xaa  Phe  Gly  Asp  Xaa  Tyr  Tyr  Thr
1                  5
```

( 2 ) INFORMATION FOR SEQ ID NO: 2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 2:

```
Phe  Asp  Trp  Asp  Ser  Thr  Lys  Tyr  Leu  Leu  Ile  Ala  Phe  Gly  Asp  Ser
1                  5                            10                           15
Tyr  Tyr  Thr  Val  Gln
                 20
```

( 2 ) INFORMATION FOR SEQ ID NO: 3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 3:

```
Thr  Thr  Lys  Tyr  Val  Ile  Ser  Phe  Gly  Asp  Asp  Tyr  Tyr  Thr  Thr  Xaa
1                  5                            10                           15
Phe
```

( 2 ) INFORMATION FOR SEQ ID NO: 4:

( i ) SEQUENCE CHARACTERISTICS:
        ( A ) LENGTH: 1315 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

```
GAATTCCAGG GACTTCCATT CGAGCCATAG CCATGCTCGC TCTCTGGCAG TGCCTAGCCC      60
TCGCGGCCAT CCCTACAGTA TCAGCATTCC CCTCCGGTTC GTCTCAGAAG GCGTTCGACT     120
GGGACTCGAC GAAATACCTA ATAGCGTTCG GTGATTCCTA TACGTACGTG CAGGGCACTC     180
ACGGACACCA AAACTATAGC TTCATTGGGG ATCTGCAGAA CTTCGCATAT GATGCTCAGA     240
CCCTGTTAAC GGATAAGATC GTTCAGAACC AGACAGCAAC GGCAGAAGGG GGCCCCAACT     300
GGGTTGAATA CCTCACCGGG TGCGGGGTAG AAGATGGAAT CATCTCACCC TTGGACTGCG     360
AGAGACAACT CTGGGACTTC GCGTTCGCGG GATCTGATAT CTCCGTTGCA TACACCCCCC     420
TCCACCACAA CTACACCGTC TCCCTCGTCA ACCAGGTCAN CCAATTCACG ACCTACGGGC     480
AGCCGGTCCT CTCGCGGCAC ATCTCCGCGC CGCAGACCCT TGTCGCCATC TGGATCGGGA     540
TCAACGACAT CGGCGACAGC GCCAAATACG CCGTCGATTT TCCGGCCTTC TACGAAACCC     600
TCATCACCAC CCTCTTCGCC TCCGTCCAGG AGATCTACGC CCAGGGCTAT CGCTCCTACC     660
TGTTCGTCAA CCTGCCGCCC CTCGACCGCA CCCCGGNCAA CCAGGCCCTG AGCCAGCCCT     720
ACCCGAACGC CACGCAGGTC GCCTGGTACA CGACGCGCT GGCCCGGAAC GCCGCCGCCT      780
TCCACCGCAA CCACACGGAC ACGGCCGTGC ACCTGTTNGA CGCGCACCGG ACGCTCAGCG     840
AGGTCATGGA CCACCCCGCG GCGTACGGCA TCGTCAACAC CACCAACTTC TGCCCCGGGT     900
ACGACCAGCC CGATATCGCG TGGAACTACC GGGCGTACGG GTGTCCGACC CCGCTGGAGG     960
AGTACTTCTG GTTCAACTCG GGGCATCTGA CGAGCCATGT GCATCAGATT CTTGCGGGTG    1020
TGTTGGAGGG GGAGCTGAGA GAGTGGTCGA AGTGAGGGTG GTCTGTCGTT GATTGGAGGC    1080
GTGGTGGGGG GAACTCATTG ATGATCCAGT GGGAATACGT CAGCTCCAAA CTATGCTTTG    1140
TACGCTTCAG TTTAGACTGA CGCAGGTAAG ACTCCGTAGC ATGATTCATC ACAACAATCC    1200
CGGACCTGCA TGCATTTAAG TTGGGTGTAT ACCACTGGTA TCTGCTTGTT ACTCCTCGTA    1260
TATGTCAACC ATATGAGAAG TCAAATATGC CATCGCGTGA AAAAAAAAAA AAAAA         1315
```

( 2 ) INFORMATION FOR SEQ ID NO: 5:

( i ) SEQUENCE CHARACTERISTICS:
        ( A ) LENGTH: 340 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 5:

```
Met Leu Ala Leu Trp Gln Cys Leu Ala Leu Ala Ala Ile Pro Thr Val
 1               5                  10                  15

Ser Ala Phe Pro Ser Gly Ser Ser Gln Lys Ala Phe Asp Trp Asp Ser
            20                  25                  30

Thr Lys Tyr Leu Ile Ala Phe Gly Asp Ser Tyr Thr Tyr Val Gln Gly
        35                  40                  45

Thr His Gly His Gln Asn Tyr Ser Phe Ile Gly Asp Leu Gln Asn Phe
    50                  55                  60

Ala Tyr Asp Ala Gln Thr Leu Leu Thr Asp Lys Ile Val Gln Asn Gln
65                  70                  75                  80

Thr Ala Thr Ala Glu Gly Gly Pro Asn Trp Val Glu Tyr Leu Thr Gly
                85                  90                  95

Cys Gly Val Glu Asp Gly Ile Ile Ser Pro Leu Asp Cys Glu Arg Gln
            100                 105                 110
```

```
Leu  Trp  Asp  Phe  Ala  Phe  Ala  Gly  Ser  Asp  Ile  Ser  Val  Ala  Tyr  Thr
          115            120                           125
Pro  Leu  His  His  Asn  Tyr  Thr  Val  Ser  Leu  Val  Asn  Gln  Val  Xaa  Gln
     130            135                      140
Phe  Thr  Thr  Tyr  Gly  Gln  Pro  Val  Leu  Ser  Arg  His  Ile  Ser  Ala  Pro
145            150                           155                           160
Gln  Thr  Leu  Val  Ala  Ile  Trp  Ile  Gly  Ile  Asn  Asp  Ile  Gly  Asp  Ser
               165                 170                           175
Ala  Lys  Tyr  Ala  Val  Asp  Phe  Pro  Ala  Phe  Tyr  Glu  Thr  Leu  Ile  Thr
               180                 185                      190
Thr  Leu  Phe  Ala  Ser  Val  Gln  Glu  Ile  Tyr  Ala  Gln  Gly  Tyr  Arg  Ser
          195                 200                      205
Tyr  Leu  Phe  Val  Asn  Leu  Pro  Pro  Leu  Asp  Arg  Thr  Pro  Xaa  Asn  Gln
     210                      215                      220
Ala  Leu  Ser  Gln  Pro  Tyr  Pro  Asn  Ala  Thr  Gln  Val  Ala  Trp  Tyr  Asn
225                      230                 235                           240
Asp  Ala  Leu  Ala  Arg  Asn  Ala  Ala  Ala  Phe  His  Arg  Asn  His  Thr  Asp
               245                      250                      255
Thr  Ala  Val  His  Leu  Xaa  Asp  Ala  His  Arg  Thr  Leu  Ser  Glu  Val  Met
               260                 265                      270
Asp  His  Pro  Ala  Ala  Tyr  Gly  Ile  Val  Asn  Thr  Thr  Asn  Phe  Cys  Pro
          275                 280                      285
Gly  Tyr  Asp  Gln  Pro  Asp  Ile  Ala  Trp  Asn  Tyr  Arg  Ala  Tyr  Gly  Cys
     290                      295                 300
Pro  Thr  Pro  Leu  Glu  Glu  Tyr  Phe  Trp  Phe  Asn  Ser  Gly  His  Leu  Thr
305                 310                      315                           320
Ser  His  Val  His  Gln  Ile  Leu  Ala  Gly  Val  Leu  Glu  Gly  Glu  Leu  Arg
                    325                 330                           335
Glu  Trp  Ser  Lys
               340
```

( 2 ) INFORMATION FOR SEQ ID NO:6:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TTGATGGGAA C         11

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CTGTAATACG ACTCACTA         18

( 2 ) INFORMATION FOR SEQ ID NO:8:

( i ) SEQUENCE CHARACTERISTICS:

-continued ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:8:

GGGCGTGAAT GTAAGCGTGA C                                      2 1